United States Patent
Brucher et al.

(10) Patent No.: US 6,425,866 B1
(45) Date of Patent: Jul. 30, 2002

(54) DEVICE AND METHOD FOR EMBOLUS DETECTION

(75) Inventors: Rainer Brucher, Lonsee; Dieter Denner, Sipplingen, both of (DE)

(73) Assignee: DWL Elektronische Systeme GmbH (DE)

( * ) Notice: Subject to any disclaimer, the term of this patent is extended or adjusted under 35 U.S.C. 154(b) by 0 days.

(21) Appl. No.: 09/463,816

(22) PCT Filed: Jul. 31, 1998

(86) PCT No.: PCT/EP98/04786

§ 371 (c)(1),
(2), (4) Date: Jan. 29, 2000

(87) PCT Pub. No.: WO99/05970

PCT Pub. Date: Feb. 11, 1999

(30) Foreign Application Priority Data

Jul. 31, 1997 (DE) .......................................... 197 33 091

(51) Int. Cl.$^7$ ................................................ A61B 8/00
(52) U.S. Cl. ................................ 600/438; 128/DIG. 13
(58) Field of Search ................................ 600/437, 438; 128/DIG. 13; 73/61.49, 865.5, 600

(56) References Cited

U.S. PATENT DOCUMENTS

| | | | |
|---|---|---|---|
| 3,762,221 A | | 10/1973 | Coulthard |
| 4,565,500 A | * | 1/1986 | Jeensalute et al. ... 128/DIG. 13 |
| 5,176,631 A | * | 1/1993 | Koenig ................. 128/DIG. 13 |
| 5,392,638 A | * | 2/1995 | Kawahara .................. 73/61.49 |
| 5,738,097 A | | 4/1998 | Beach et al. |

* cited by examiner

Primary Examiner—Francis J. Jaworski
(74) Attorney, Agent, or Firm—Piper Rudnick

(57) ABSTRACT

A device for detecting embolus uses ultrasonic signals reflected on a fluid flow in a body. The device features a first ultrasonic unit for receiving a first signal generated in a first position in a vessel and a second ultrasonic unit for additional reception of a second signal generated in a second position in the body. The device also features a detector unit for detecting the embolus. The detector unit is triggered only if the time interval between the characteristic changes in the first and second signal, corresponding to a possible embolus, exceeds a minimum value, or if the characteristic signal change occurs in one of the signals only.

9 Claims, 3 Drawing Sheets

DEVICE AND METHOD FOR EMBOLUS DETECTION

FIELD OF THE INVENTION

The present invention concerns a device for embolism detection as set forth in the classifying portion of claim 1, and a method of embolism detection.

BACKGROUND OF THE INVENTION

Such devices and methods of the general kind set forth are used in medical ultrasound diagnostics in order on the basis of the reflected ultrasound Doppler signals and in particular changes therein to be able to draw conclusions about foreign bodies which are disposed in a blood vessel. It is known that in particular embolisms or comparable foreign bodies are distinguished by a reflection characteristic in respect of the introduced ultrasonic signal, that is greatly different in comparison with a surrounding fluid medium—for example blood—, so that these particularities are used for embolism detection.

In that respect, the state of the art includes devices which, by suitable demodulation of the received reflected Doppler signal and subsequent acoustic output afford an operator—for example a doctor dealing with the case—an acoustic way of detecting an embolism. The latter is expressed in the acoustic output signal by virtue of a characteristic noise.

In addition the state of the art discloses apparatuses which also prepare an ultrasonic signal reflected from a flow of blood, for optical display and evaluation. Those apparatuses are distinguished in that a received ultrasonic signal which is reflected at the flow of blood in a vessel is demodulated and subsequently prepared by means of digital image processing in such a way that a spectral representation of the ultrasonic signal (of the motion signal) in relation to time can be obtain for example on a surveillance monitor. Especially provided processors implement in that respect the necessary steps for image generation, in particular Fourier transformation of the received data. In that way then a detected foreign body would be visually represented on the display screen, for example by virtue of coloured emphasis of the characteristic signal amplitude of the embolism signal in the surrounding flow of blood in the spectral representation.

In practical operation however it has been found useful to effect the detection of foreign bodies in the blood stream in a more precise manner and in particular also to make it possible to distinguish embolisms from so-called artefacts, more specifically signal disturbances of an ultrasonic probe which is used for the methods and devices of the general kind set forth—as occur for example due to movements of the probe; more specifically, just like an embolism, an artefact results in a characteristic signal change in an optical or acoustic output signal of the device and, in the case of an artefact, would impair diagnostic accuracy and result in the operator being unnecessarily distracted.

The specific task of distinguishing an embolism or the like foreign body in the bloodstream from an artefact was approached in various ways in the state of the art. Thus for example the teaching of U.S. Pat. No. 5,103,827 makes use of the properties of an artefact (in comparison with an embolism) that, in the case of an artefact, the image representation or display involves a bi-directional spectral signal (both in a positive and also a negative direction) which can be distinguished from a uni-directional embolism signal by virtue of suitable circuitry measures and measures relating to signal processing procedures. However such a solution, due to the necessary variable thresholds for distinction purposes and the complication and expenditure which this entails, is only limitedly suitable for affording a simple and convenient way of distinguishing embolisms. In addition it is precisely in relation to relatively large embolisms that the problem arises that—for example due to over-driving of interposed amplifier units—such relatively large embolisms also result in a bi-directional spectral representation so that in that respect the path adopted cannot in any case lead to a satisfactory result.

In addition U.S. Pat. No. 5,348,015 describes a further approach for distinguishing an artefact from an embolism. In particular the inventors here propose using a multi-channel device which is operated at various frequencies for embolism detection and distinction. As more specifically the ultrasonic reflection properties in particular of an embolism are frequency-dependent, that affords a secure way of distinguishing same for example from an artefact (which is uninfluenced thereby). More specifically, in the case of an embolism—in contrast to an artefact—a signal (amplitude) strength which is different for various ultrasonic frequencies is to be established in the spectral representation, and that strength can then be evaluated. It will be noted however that the device described in U.S. Pat. No. 5,348,015 is extremely complicated and expensive and, besides a plurality of transmitting and receiving channels (that is to say signal generation, reception and demodulation are respectively required separately), the device also requires special probes which are suitable for a multi-frequency mode of operation, and in addition it gives rise to considerable difficulties in regard to control and software engineering. In particular from the point of view of inexpensive and uncomplicated implementation of reliable embolism detection and distinction therefore, this approach also appears to suffer from disadvantages.

BRIEF SUMMARY OF THE INVENTION

The object of the present invention is therefore that of improving a device for embolism detection of the general kind set forth, in such a way that detection of an embolism and in particular distinction thereof from an artefact can be effected in a more reliable and simpler fashion. The invention also aims to provide a suitable embolism detection method.

That object is attained by the device having features of claim 1 and the method as set forth in claim 9.

The device according to the invention advantageously makes it possible to reliably distinguish an embolism from an artefact on the basis of two signals which are evaluated in respect of their respective signal changes—which could indicate an embolism—and the time interval between those signal changes.

In that respect the invention makes use of the principle that an artefact, produced for example by movement of the ultrasonic probe in the position of attachment to the head and as an interference signal in the two signals to be evaluated occurs substantially simultaneously or however only with a minimum time interval. In comparison an embolism is made distinguishable by virtue of the fact that, when reaching the first position in the (blood) vessel, it produces the characteristic signal change for example arise in amplitude—while this still cannot be the case at the second position which is different from the first position, at that moment in time. On the contrary, at the second position, if this is also in the same vessel, the characteristic signal change occurs in respect of time prior to or after the first signal change, in dependence on how the first and second positions are arranged relative to each other in the direction of flow of the fluid (the embolism moves with the speed of flow of the fluid in the vessel) so that the time interval between the respective signal changes corresponds to the duration of transportation between the two positions. If the second position is arranged outside the vessel, then in the normal case no characteristic signal change in the second signal is produced by the embolism in the vessel.

In that respect, in connection with the invention, the ultrasonic transmitting device may have one or a plurality of ultrasonic probes.

Advantageous developments of the invention are set forth in the appendant claims.

Thus it is particularly preferred for the second position to be arranged outside the vessel to be monitored; in a further preferred feature that position—when implementing monitoring on the head of a patient—is at a depth of between about 30 and about 35 mm in relation to the surface of the head and directed onto a skull bone.

In that way there is then practically no change in the second signal—that is to say in the reference channel—when an embolism passes the first position and thereupon the first characteristic signal is generated.

It is also to be assumed that the minimum time interval in use in a practical medical context is practically zero and even theoretically does not exceed between 2 and 3 msec.

Advantageously there is provided a so-called gating system for embolism detection according to the invention, more specifically evaluation, displaced in respect of time, of the same reflected transmitting signal, whereby observation of two different depths of penetration in the body is made possible. In accordance with the invention a first depth of penetration is set to the first position while preferably the depth of penetration which determines the second position is outside the vessel. It is also in accordance with the invention to provide a plurality of gates—which are for example graduated or stepped in terms of the depth of penetration—and of which then at least one is to be used as a reference gate to be employed to generate the second signal.

While moreover operation of the detector unit is usually implemented on the basis of first and/or second signals which are transformed into the time domain (that is to say FFT), embolism detection and distinction is in principle also possible in the time domain in accordance with the invention; it is advantageously possible in that way to save on an FFT-processor at least for the reference channel.

Further advantages, features and details of the invention will be apparent from the description hereinafter of specific embodiments and with reference to the drawings in which:

DETAILED DESCRIPTION OF THE INVENTION

Figure 1:
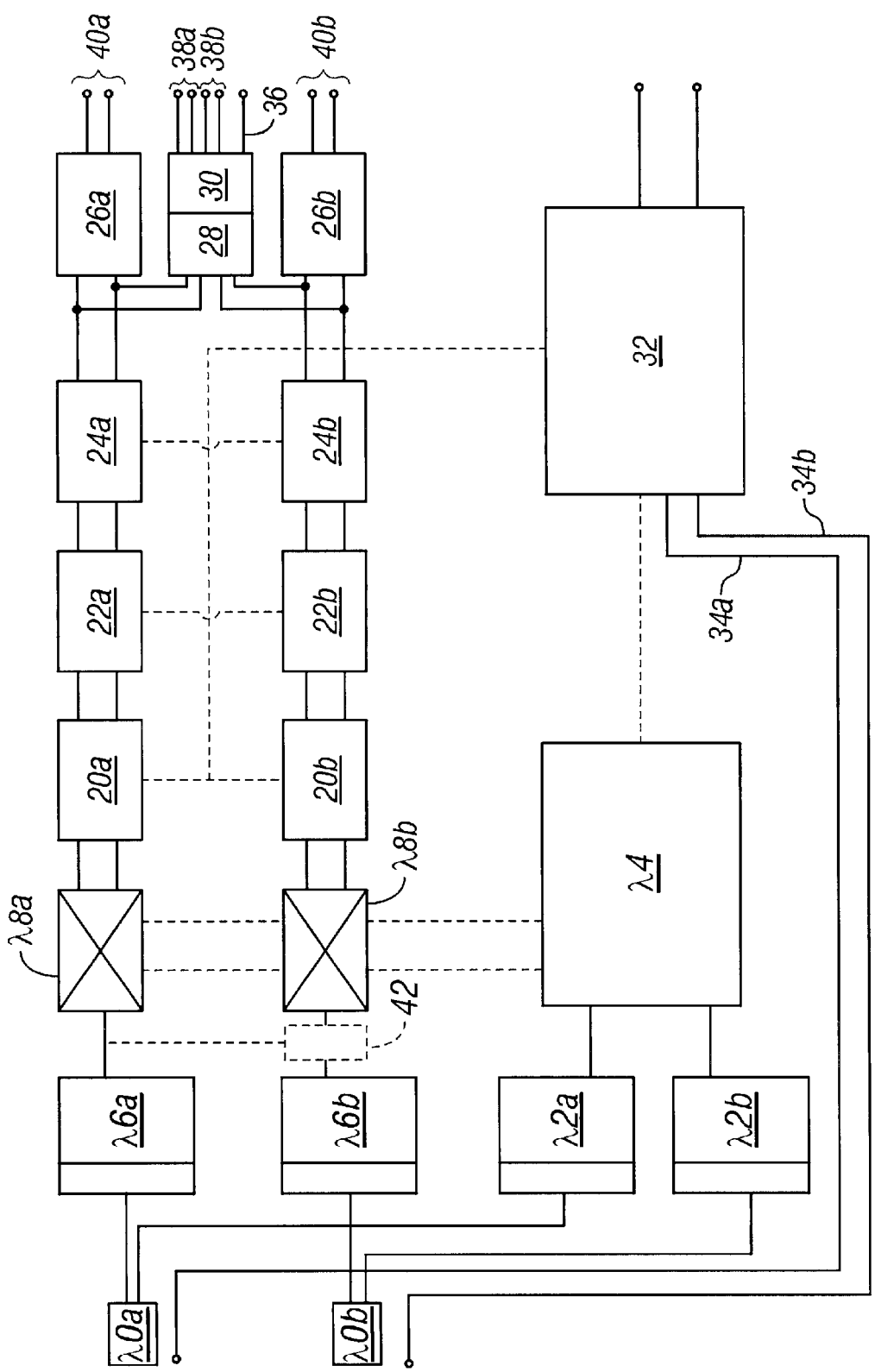
FIG. 1 shows a block circuit diagram of the device according to the invention for embolism detection in accordance with a first embodiment with two mutually independent probe units.

The block circuit diagram in FIG. 1 shows the detection part of a device for embolism detection in accordance with a first preferred embodiment of the invention (best mode). The arrangement has two mutually independent probe channels (indicated in the Figure by the indices "a" for the first channel and "b" for the second channel) which respectively generate separately in themselves an evaluatable ultrasonic Doppler reception signal, which is then used in the procedure according to the invention for embolism detection or distinction.

A first probe $10a$ is connected on the transmitting side to a first multiplexing and transmitting unit $12a$ which is designed for current frequencies of ultrasonic sonography, for example 2, 4, 8 or 16 MHz, and which is connected to an oscillator module $14a$ disposed upstream thereof.

On the receiving side an output signal of the first probe $10a$ is applied to a first multiplexing and pre-amplifier unit $16a$, is subsequently processed by a first mixer and demodulator unit $18a$, and is passed to a first (programmable) high pass filter $20a$. In the arrangement shown in the block circuit diagram, the filter $20a$ is followed by a first adjustable amplifier $22a$ ("programmable gain") whose output signal is processed by a first sample-and-hold (S & H) circuit $24a$.

The signal produced in that way is then applied on the one hand to a first audio filter $26a$ for signal output for an embolism signal which is to be acoustically evaluated, and on the other hand a common FFT-processing unit 28 (FFT= Fast Fourier Transformation) receives the output signal of the first sample-and-hold circuit $24a$ for processing of the visual representation of the Doppler signal as a spectral representation in relation to time. The FFT-processing unit 28 has a common detector unit 30 connected downstream thereof.

The parallel second channel which is connected to the second probe $10b$ is of a structure corresponding to the above-described first channel, more specifically by means of a second transmitting unit $12b$ which is also controlled by the oscillator 14, and on the receiving side by means of multiplexer/pre-amplifier unit $16b$, mixer $18b$, high pass filter $20b$, amplifier $22b$ and sample-and-hold circuit $24b$ whose signal is again passed on the one hand to a second audio filter $26b$ and on the other hand is also applied to the common FFT-processing unit 28.

A common control unit 32 which is implemented by means of a microcontroller provides on the one hand for control of the first and second high pass filters $20a$, $20b$, the first and second intermediate amplifiers $22a$, $22b$ and the two sample-and-hold circuits $24a$, $24b$ and in addition provides for control of the oscillator unit 14. The latter in turn controls the mixer units $18a$, $18b$ provided for quadrature demodulation. In addition, associated with each probe $10a$, $10b$ is an identification signal line $34a$, $34b$ for the control unit 32.

With the exception of the common FFT-processing unit 28 and the detector unit 30, the circuit which has been described hereinbefore is a current product, as is offered by the applicants for example under the name "Multi-Dopp" as a two-channel system for medical ultrasonic diagnostics.

In a manner which is advantageous in accordance with the invention however, the invention provides that drawing a distinction between an embolism and an interference signal to be suppressed, for example an artefact, is effected in the detector unit 30, by evaluation of a respective reception signal—in the illustrated embodiment, after a Fourier transformation operation, that is to say in relation to a signal in the frequency region.

In the manner which is advantageous according to the invention, the detector unit 30 is designed as an electronic unit for digital signal processing, in such a way that an artefact which is expressed in both channels as a substantially simultaneous, marked rise in amplitude of the reception signal, is recognised as such by virtue of the relationship in respect of time between the channels and consequently no embolism detection signal is outputted on a detector signal output 36.

To put this more precisely, for example a movement of the probes which can be secured by means of a suitable support unit to the human body, for example on the head, results in an unwanted, high-level reception signal, caused by such movement, in both probes, occurring practically simultaneously (or within a time interval of less than 3 ms). The reception signal in both channels, which is further processed in accordance with the processing units in the block circuit diagram of FIG. 1, is then to be identified as simultaneous by the common detector unit, whereupon then the conclusion is drawn that an artefact is involved. In comparison for example the occurrence of an embolism in a detection region of the first probe (which is suitably directed for example onto a region of a blood vessel) would result in a (high-level) signal while the second probe which is directed onto another region of the blood vessel, onto a region of tissue or bone outside or however onto another vessel (or which for example in the case of measurement on the head is disposed on the opposite end) would not detect the embolism detected in the first channel. For that reason, a detection signal of high amplitude admittedly occurs in the first channel but not in the second channel (or, in the case of spatial displacement of the two detection regions of the probes in the same vessel, at a time interval corresponding to the transportation speed in the flow of blood). In a corresponding manner it is possible by means of the detector unit to establish that a characteristic rise in signal has not occurred at the same moment in time in both channels so that it is possible to conclude that an embolism is involved.

As FIG. 1 shows FFT-outputs 38*a*, 38*b* are provided for subsequent visual signal representation of the transformed signals of the signal channels which are designed in the known and usual manner, and in addition an operator handling the device can acoustically monitor the respective channel by way of audio outputs 40*a*, 40*b* of the first and second audio filters 26*a*, 26*b* respectively.

An additional gate and multiplexer unit 42 which is shown in broken line and which is connected downstream of the second pre-amplifier unit 16*b* implements a development of the embodiment shown n FIG. 1: more specifically, the additional unit 42, as indicated by the further line shown in broken form, also receives the output signal of the first pre-amplifier 16*a*, triggering the function of the gate and multiplexer unit 42. In accordance with the output signal of the first pre-amplifier 16*a*, the unit 42 produces a certain time delay in regard to sampling for the second channel (b) whereby—due to the different transit time—another detection region (more precisely: another detection depth) is afforded for signal preparation in the second channel. The reference signal formed in that way (considered as the "gate" in accordance with the time displacement) is then, in the described manner, along the second channel, mixed and demodulated (18*b*), filtered (20*b*), amplified (22*b*) and sampled (24*b*) so that the output signal of the probe 1 occurs at the common FFT-processing unit in duplicate—produced on the one hand by the first channel and on the other hand produced by the second channel, displaced by the gate spacing.

The output signal of the second channel therefore corresponds to a displacement in respect of location of the detection depth with respect to the first channel, wherein that displacement—depending on the respective setting of the multiplexer/gate unit 42—can lead or trail the first channel, in regard to a depth of penetration. In particular the gate provided in that way can also be set in such a fashion that the (reference) gate signal produced by means of the multiplexer/gate unit 42 does not fall into the vessel which is being monitored in the first channel, but for example on a bone or a piece of tissue adjacent to the vessel. In that case no high-level detection signal will be outputted in the second channel which is additionally used as a reference, if an embolism in the blood vessel produces a signal change in the first channel, so that then the existence of an embolism can be correspondingly reliably established.

Figure 4:
FIG. 4 shows a signal diagram with a representation of three signal configurations in relation to time for embolism distinction.

FIG. 4 shows a usual transit time or depth setting which is suitable in particular also for operation of the device shown in FIG. 1. While both the detection region for the first channel a (uppermost signal in FIG. 4) and also for the second channel b (second signal in FIG. 4) are put to a depth of between about 40 and 45 mm from the probe surface—in the illustrated embodiment measurement is effected by way of the channels a and b on both sides of the head—the reference signal in the first channel $a_{REF}$ is put to a depth region of between 30 and 35 mm, when carrying out measurements on the head near the skull bone of the patient and in dependence on the respective anatomy involved. As the trigger or clock signals in FIG. 4 show therefore in the case of an embolism—which would not be detected in the reference gate as with positioning on the bone the latter is outside the vessel—only the first channel would generate an embolism detection signal but the reference channel and the second channel would not. In comparison an artefact would occur equally in the signal channel a and in the reference channel $a_{REF}$. The gate therefore produces a delay corresponding to a depth of penetration, which is different in relation to the signal channel, due to the varying transit time.

Figure 2:
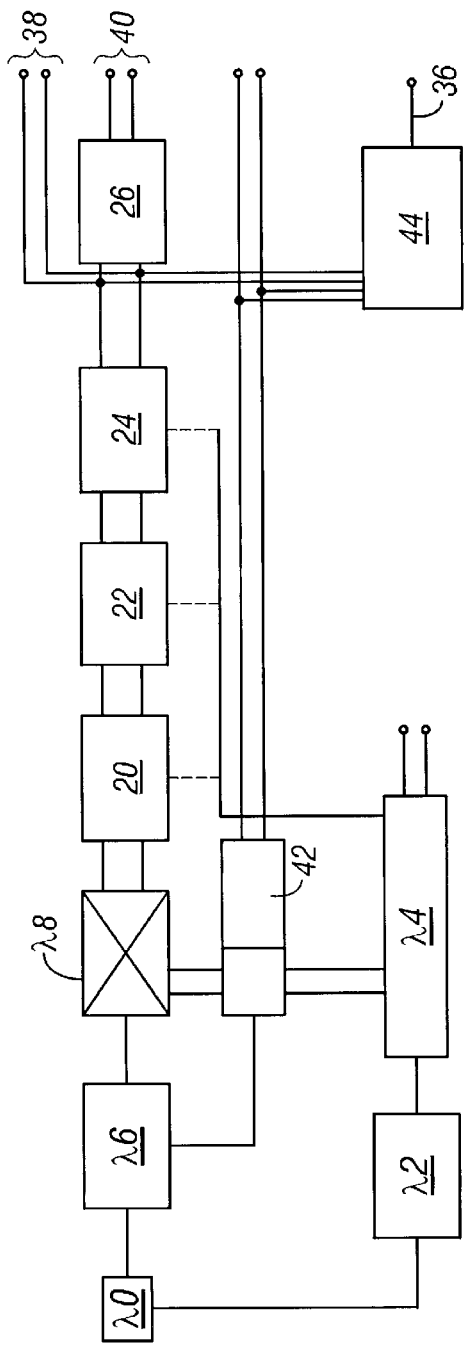
FIG. 2 shows an alternative embodiment of the invention with an individual probe unit, for which there is provided a reference gate.

FIG. 2 illustrates a block circuit diagram showing a simplified embodiment which is slightly modified in relation to the embodiment of FIG. 1. Corresponding functional elements are denoted by references corresponding to those used in FIG. 2, FIG. 2 having a first complete signal channel which at the end in turn has an FFT-output 38 and an audio output 40 while the reference gate is not in the form of a complete signal channel but only in the form of a mixer/gate unit connected downstream of the pre-amplifier 16, corresponding to the unit 42 in FIG. 1. This simplified Doppler channel does not require the further, downstream-disposed signal preparation operation for it is only required for detection and distinction of an artefact (and not for example for further calculation and representation of a Fourier-transformed spectral imaging).

Accordingly the detector module 44 detects both the reception signal of the first channel and also the signal of the reference channel, which is outputted by the gate unit 42, and produces therefrom a detector output signal for the detector signal output 36 when in the above-described manner a characteristic amplitude signal occurs at the output of the sample-and-hold circuit 24, but a corresponding signal does not occur at the same moment in time at the output of the reference gate 42.

Figure 3:
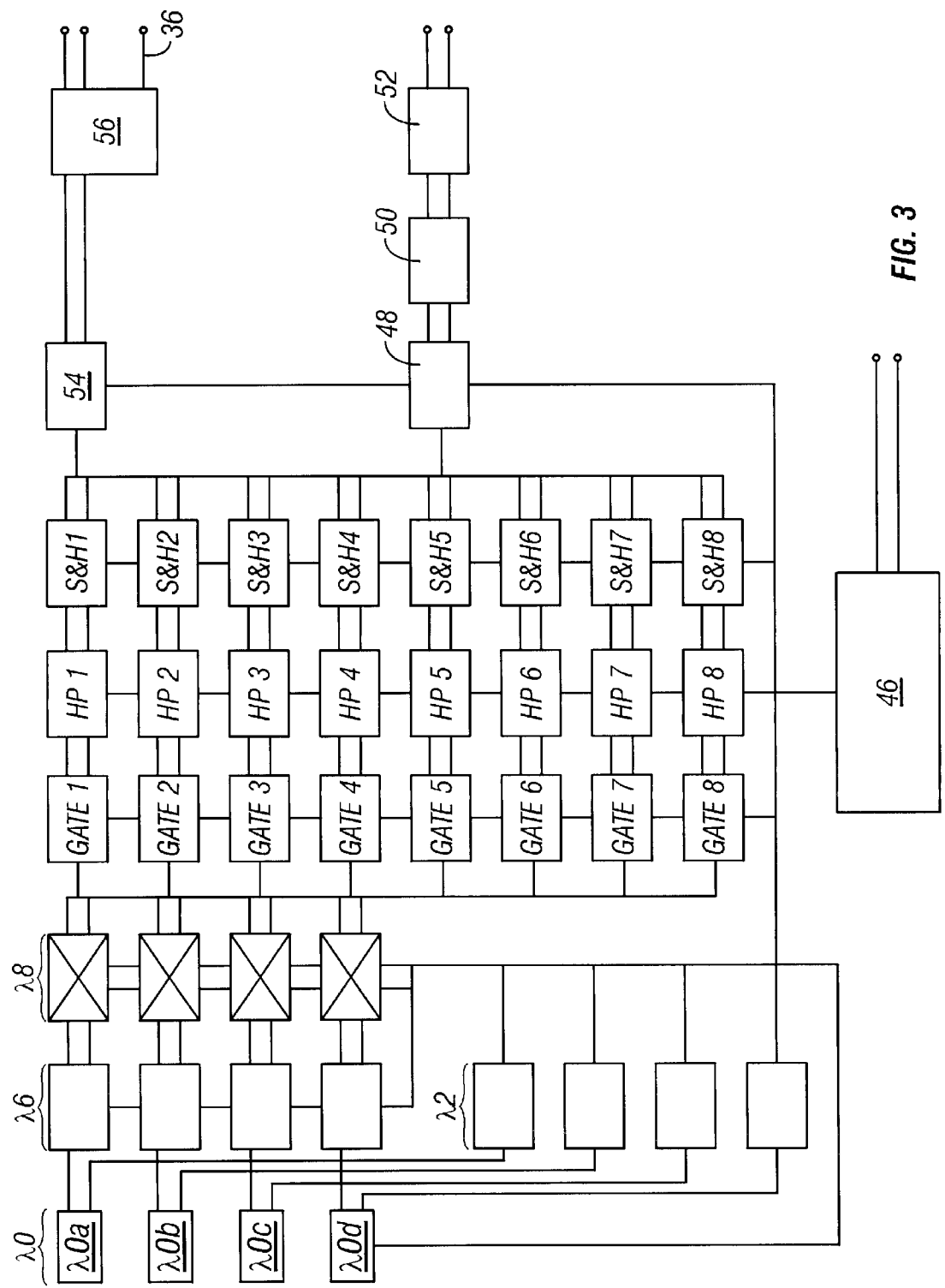
FIG. 3 shows a block circuit diagram of a further embodiment of the invention which provides a multi-gate system with up to four probes and up to eight gates which are to be associated in any desired manner with the probes, at least one of said gates serving as a reference gate for embolism distinction.

FIG. 3 shows a further embodiment of the present invention, more specifically in the device shown in FIG. 3 a total of up to four different probes 10a through 10d (corresponding to a respective one of four channels a, b, c, d) can be connected, which at the transmitting side are acted upon by transmitting units 12a through 12d and which on the receiving side are tapped off by pre-amplifiers 16a through 16d with mixer/demodulator units 18a through 18d connected on the output side thereof. Connected downstream of the mixer units as a multiplex arrangement are eight gate channels each comprising a controllable gates, a high pass $HP_i$ and a sample-and-hold circuit $S\&H_i$ (in each case i=1 . . . 8). Control and variable, individually settable association of the respective gate channels with the four probe channels is implemented by the action of a gate control unit 46 which is in the form of a suitably designed controller. That control unit which has an oscillator portion also controls the transmitting units and the receiving units which are connected upstream of the gate units; the multiplex audio output, comprising audio multiplexer 48, equalizer 50 and audio processor 52, as well as an FFT-processing unit 54 for further processing and output of the signals for visual representation are supplied with control signals by the control unit 46.

Connected downstream of the FFT-processing unit 54 once again is an embolism detector unit 56 having a detector signal output 36 which in the above-described manner, from the FFT-transformed gate signals which occur in the form of a multiplex signal, evaluates at least one of the eight gates as a reference gate and from the signal configurations concludes the occurrence of an embolism (as distinct from an artefact).

The embodiment illustrated in FIG. 3 permits in a highly flexible manner the use of up to four different probes, wherein, similarly to the mode of operation as described with reference to FIG. 1 or FIG. 2, a single probe also already permits complete embolism detection operation in accordance with the present invention, as long as at least one of the eight gate channels is set up in the above-described manner as a reference channel and in particular is directed onto a differing (reference) detection region outside a vessel to be monitored. The remaining gates can then monitor for example in graduated or staggered fashion different depths of a vessel. Alternatively, it would be possible to envisage a configuration in which there are provided for example two probes each with four gates which are stepped in respect of depth, wherein in each case at least one of the four gates is set as a reference gate.

The detector unit 56 diagrammatically illustrated in FIG. 3 is then appropriately suitably set or programmed for signal evaluation purposes.

It will be seen from the foregoing discussion that the invention can be carried into effect in various ways, in which respect in particular it is also not necessary that an FFT-transformation procedure or the like operation always has to be effected with the received ultrasonic signal, prior to detection of an embolism (linked to distinguishing it from an artefact, in accordance with the invention). On the contrary it is certainly possible, see for example the original embodiment of FIG. 1, to implement that distinguishing operation solely in the time domain or region of the signals which are detected or which are to be compared. A corresponding consideration applies in regard to the provision of reference gates which, by virtue of the change in accordance with the invention in the detection time of the reflected signal, reflect the state of a detection region in the body, which is a different region (due to the transit time involved). It is assumed that the best distinction between embolism and artefact, in accordance with the invention, is possible when the detection region for the additional reference channel is set at a location outside the blood vessel to be observed, because in that way mutual influencing of the channels is substantially avoided. In the above-indicated fashion however it is in principle also possible to provide for detecting and distinguishing an embolism if the signals to be evaluated represent two different detection locations in the same vessel.

All in all therefore embolisms can thus be reliably distinguished from artefacts in the described fashion, in which respect laboratory tests have shown that—compared to known methods of embolism detection—markedly improved success rates can be achieved.

If the detection region for the reference channel is set to a location outside the vessel to be observed, then in the case of an actual embolism in the vessel there is practically no signal input into the second (reference) channel; any coupling or cross-talk effects are expressed at best in only slightly rising amplitudes in the reference channel.

Checking using measurement procedures has also shown that an artefact always occurs practically simultaneously in both channels and leads there in measurable signal changes; at the longest, a time delay between the channels is up to three ms, and is therefore markedly below the time settings which are used by way of example in accordance with the present invention.

What is claimed is:

1. A device for embolus detection by means of ultrasonic signals which are reflected at a flow of fluid in a body, comprising:

an ultrasonic unit which is adapted for periodically producing ultrasonic monitoring signals for a suitably designed ultrasonic transmitting device and for receiving a first signal reflected at a first position corresponding to the flow of fluid in a vessel;

a signal evaluation unit which is connected downstream of the ultrasonic unit for preparing and visually and/or acoustically providing the reflected first signal;

a detector unit which co-operates with the signal evaluation unit and which is adapted to detect an embolus in the flow of fluid and to output a detection signal as a reaction thereto;

wherein the ultrasonic unit is designed for additionally receiving a second signal from the ultrasonic transmitting device, which is reflected at a second position in the body that lies outside the vessel and the flow fluid; and the detector unit is designed to detect an embolus as a reaction to the first and the second signal in such a way that output of the detection signal occurs only if a characteristic signal change, corresponding to a possible embolus, in one of the first and second signals occurs outside a minimum time interval from a signal change in the respective other signal, or the characteristic signal change occurs in only one of the signals.

2. The device set forth in claim 1 wherein the minimum time interval is three msec.

3. The device set forth in claim 1 wherein the ultrasonic unit is so adapted that the second signal is generated at a moment in time which is different from the first signal in accordance with a different depth of penetration of the ultrasonic signal into the body, from a common transmission signal.

4. The device set forth in claim 1 wherein the first signal is produced from a first ultrasonic probe unit as a signal source and the second signal is produced from a second ultrasonic probe unit as a further signal source.

5. The device set forth in claim 1 wherein the ultrasonic unit is so adapted that the second position is in the head region and at a depth, relative to an associated ultrasonic transducer, of between about 30 and 35 mm, and the first position is at a depth of greater than 40 mm.

6. The device set forth in claim 1 wherein the ultrasonic unit on the receiving side is of a multi-channel configuration with a plurality of receiving units which are adapted to output discrete signal states of the first and/or the second signal and which can be controlled in time-displaced relationship as a reaction to a common transmission signal.

7. The device set forth in claim 1 wherein the detector unit implements processing of the first and the second signals for detecting the embolus in the time domain.

8. The device set forth in claim 1 wherein the detector unit is so adapted that processing of the first and the second signals for detecting the embolus is effected on the basis of at least one signal which is transformed into the frequency domain.

9. A method of embolus detection by way of ultrasonic signals which are reflected at a flow of fluid in a body, comprising the following steps:

periodically emitting ultrasonic vessel monitoring signals by way of a suitably adapted probe;

receiving and preparing the signals reflected at a flow of fluid in a vessel to be observed, and evaluating the prepared signals and outputting a detection signal for a detected embolus as a reaction to the received signals;

additionally receiving a reference signal which is reflected at a position in the body outside the vessel to be observed; and comparing the reference signal to the signals reflected at the flow of fluid and determining an embolus as a reaction to the existence of a characteristic signal change, corresponding to an embolus, in the reference signal and/or as a reaction to a time interval between the characteristic signal change in the reference signal and a corresponding signal change in the signals reflected at the flow of fluid.

\* \* \* \* \*